United States Patent [19]
Matsushita

[11] Patent Number: 5,827,723
[45] Date of Patent: Oct. 27, 1998

[54] NEUTRALIZING MONOCLONAL ANTIBODY 0.5β WHICH BINDS AN EPITOPE LOCATED WITHIN THE REGION OF AMINO ACIDS 308-331 OF HTLVIIB GP120

[75] Inventor: Shuzo Matsushita, Kumamoto-ken, Japan

[73] Assignee: Kyowa Hakko Kogyo Co. Ltd., Tokyo, Japan

[21] Appl. No.: 972,890

[22] Filed: Nov. 6, 1992

Related U.S. Application Data

[63] Continuation of Ser. No. 618,033, Nov. 27, 1990, abandoned, which is a continuation of Ser. No. 198,957, May 26, 1988, abandoned.

[30] Foreign Application Priority Data

Jul. 29, 1987 [JP] Japan .................................. 62-133909

[51] Int. Cl.$^6$ .............................. C12N 5/20; C07K 16/08; G01N 33/53
[52] U.S. Cl. ................. 435/240.27; 530/388.35; 435/78.21
[58] Field of Search .................... 530/388.35; 435/172.2, 435/70.21, 240.27, 7.21; 424/85.8, 148.1

[56] References Cited

U.S. PATENT DOCUMENTS 4,863,730   9/1989   Karpas .

OTHER PUBLICATIONS

Fahey et al. Clin Exp. Immunol 88:1–5, 1992.
Kipps et al. in Weir et al. *Handbook of Experimental Immunology* vol. 4 Blackwell Scientific Publ., 1986 pp. 108.1–108.9.
Bolognesi et al. J. Acquired Immune Deficiency Syndromes; 3:390–394, 1990.
Skinner et al. AIDS Research and Human Retroviruses 4:187–197, 1988.
Putney et al. Science 234:1392–1395, 1986.
Emini et al. J Virology 64:3674–3678 1990.
Devash et al. PNAS 87:3445–3449, 1990.
Matsushita J Virology 62:2107–2114, 1988.
Thomas et al. AIDS 2:25–29 1988.
Linsley et al. J Virology 62:3695–3702 1988.
Skinner et al. J Virology 62:4195–4200 1988.

*Primary Examiner*—Paula K. Hutzell
*Attorney, Agent, or Firm*—Schweitzer Cornman & Gross

[57] ABSTRACT

The present invention relates to monoclonal antibody 0.5β which binds to an epitope located within the region of amino acids 308–331 of HTLVIIIB gp120 and is capable of substantially neutralising the activity of human immunodeficiency viruses, to a hybridoma which produces the 0.5β antibody, to processes for preparing them and to compositions containing an effective amount of the antibody.

3 Claims, 4 Drawing Sheets

FIG.3A  FIG.3B  FIG.3C  FIG.3D  FIG.3E
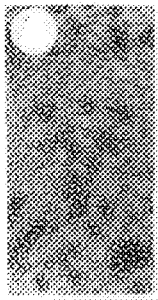 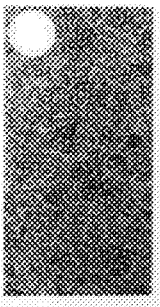 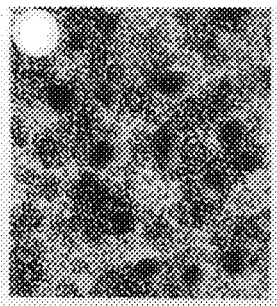 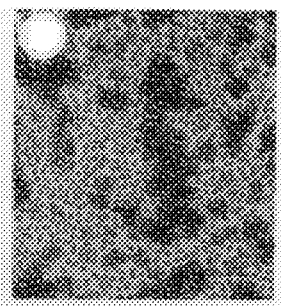 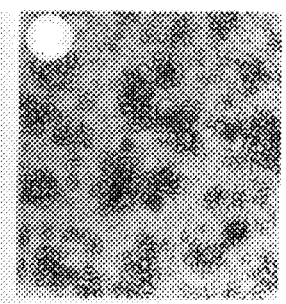
 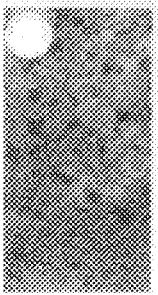  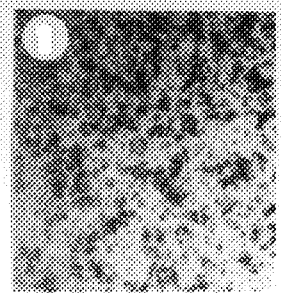 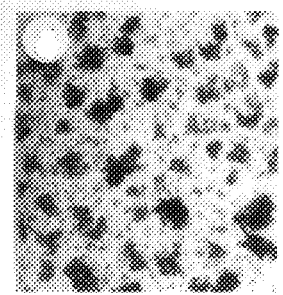
FIG.3F  FIG.3G  FIG.3H  FIG.3I  FIG.3J

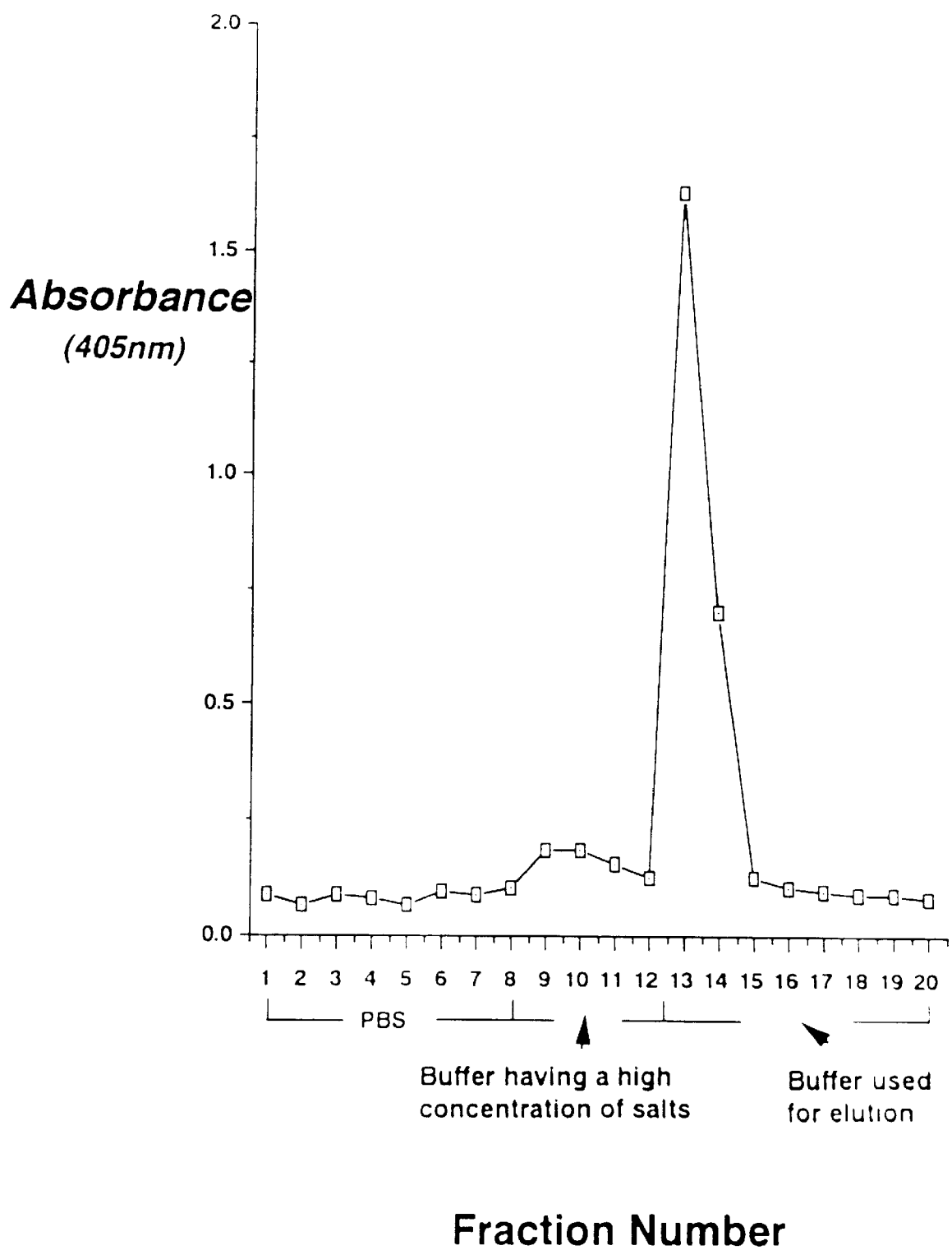

NEUTRALIZING MONOCLONAL ANTIBODY 0.5β WHICH BINDS AN EPITOPE LOCATED WITHIN THE REGION OF AMINO ACIDS 308-331 OF HTLVIIB GP120

This is a continuing application of abandoned U.S. Ser. No. 618,033, filed on Nov. 27, 1990, now abandoned which is a continuation application of U.S. Ser. No. 198,957, filed on May 26, 1988, now abandoned.

BACKGROUND OF THE INVENTION

1. Field of the Invention

The present invention relates to monoclonal antibodies capable of neutralizing human immunodeficiency viruses.

2. Description of the Prior Art

Human immunodeficiency virus (HIV) is a human retrovirus which is an etiological factor for the Acquired Immunodeficiency Syndrome (AIDS) and related disorders such as Aids Related Complex (ARC). Nowadays, AIDS is well known as a world-wide epidemic, for which no effective vaccine or cure has yet been presented. The most profound hematologic feature associated with AIDS is the functional impairment and quantitative depletion of the helper/inducer subset of T-lymphocytes which express the CD4 surface antigen. HIV-induced immunosuppression results in a variety of deficiencies of the host defense system which render the body highly susceptible to opportunistic infections such as pneumocystic carinii pneumonia and unusual neoplasms such as Kaposi sarcoma. The immune defect appears to be progressive and irreversible and reslts in a very high mortality rate which is likely to approach 100% over a number of years.

In the first stage of infection of HIV to T cells, cell-free infection viz. attachment of cell-free virons to the target receptor CD4 antigen, occurs. However, HIV may also spread by cell-to-cell infection viz. by fusion of infected T cells with uninfected T cells so that the formation of syncytia (multi-nucleated giant cells) occurs in the organs such as the brain and the lymph nodes. Furthermore, the formation of syncytia may be observed in an in vitro assay. The depletion of CD4 possitive cells may occur because the HIV-infected T cells are susceptive to the cytopathic effects of HIV.

It is known that HIV infects not only to the helper/inducer subsets of T cells but also to the cells of the monocyte/macrophage lineage. It was also known that most of monocytes/macrophages and certain T cells are resistant to the cytopathic effects of HIV and are thus considered to act as the reservior cells of the viruses.

As is well known, prototype HIV are human T-lymphotropic virus type III (HLTV-III) and lymphoadenopathy associated virus (LAV).

It is further known that polyclonal antibodies against HIV are present in sera obtained from HIV-infected humans, but the neutralizing activities of such antibodies are, in general, very weak. [reported, for example, by Weiss, R. A. et al, Nature, 316, 69–72 (1985)].

The exisitence of certain structural antigens of HIV including core (gag) antigens and envelope antigens are well known. The viral envelope comprises a 160 kilodalton (gp160) precursor glycoprotein which is subsequently cleaved into 120 kd (gp120) and 41 kd (gp41) glycoproteins present on the viron particle. The external envelope protein of HIV gp120 is the most important glycoprotein with respect to the following characteristics:

(1) Gp120 and/or certain fragments of gp120 are capable of inducing polyclonal neutralizing antibodies in experimental animals. This means that gp120 is at least one of the target molecules of neutralizing antibodies [as disclosed, for example, in Lasky. L. A. et al. Science, 233, 209–212 (1986): Robey, W. G. et al. Proc. Natl. Acad. Sc. U.S.A., 83, 7023–7027 (1986) and Putney S. D. et al, Science, 234, 1392–1395 (1987)].

(2) The infection of HIV is initiated by binding of gp120 to the receptor CD4 molecule. This means that gp120 is a critical molecule for HIV with respect to the infection to target cells [as disclosed, for example, in McDougal J. S. et al, Science, 231, 382–385 (1986)].

(3) The formation of syncytia induced by HIV viz. the cell-to-cell infection of HIV depends on the direct interaction of gp120 with CD4 molecules of the uninfected cells [as disclosed, for example, in Lifson J. D. et al, Nature 323, 725–728 (1986)].

Various monoclonal antibodies against the protein components of HTLV-III or LAV have hitherto been proposed, as exemplified by those against p24, one of the core antigens present on the inside of the viruses [Veronese F. D., Proc. Natl. Acad. Sci. USA., 82, 5199–5202(1985): those against the product from the pol gene capable of coding the reverse transcriptase of the viruses [Veronese F. D. et al., Science 231, 1289–1291 (1986); and those against gp41, part of the envelope [Veronese F. D. et al. Science 229, 1402–1405 (1985). However, none of these antibodies are capable of reacting with gp120 antigen which is important for preventing and treating AIDS. It has been reported that no monoclonal antibody capable of effectively neutralizing gp120 was observed by immunization with purified LAV [for example, Chassagne J. et al, J. Immunol. vol. 136, 1442–1445 (1986).

Various attempts have been made to provide monoclonal antibodies which are capable of effectively neutralizing AIDS viruses and which may be used for diagnosis and treatment of AIDS.

Recently, it has been reported that a monoclonal antibody capable of reacting with gp120 may be obtained by using a synthetic peptide as immunogen [Chanh T. C. et al, Eur. J. Immunol., 16: 1465–1468 (December 1986)]. The epitope recognized by this monoclonal antibody is located within amino acid sequence 503 to 532 of HIV gp160, the amino acid sequence of HIV being determined with reference to Ratner I. et al. Nature, 313: 277–284 (1985). However, the binding activity of this monoclonal antibody is weak when determined by the Western blot method and the surface immunostaining of HIV-infected cells. Moreover, no evidence of the neutralizing activity of this monoclonal antibody is shown in this report.

The present invention is based upon the discovery that the monoclonal antibodies which I have prepared are capable of significantly neutralizing (hereinafter defined) HIV by binding with an epitope of the HIV envelope antigens.

The present invention is directed to provide monoclonal antibodies capable of substantially neutralizing HTLV-III and LAV viruses and to hybridoma for the preparation of such monoclonal antibodies.

The term neutralizing used herein denotes the inhibition of HIV infection by cell-free virons and/or the inhibition of cell-to-cell infection such as the formation of syncytia by the fusion of HIV-infected cells with uninfected cells induced by the interaction of gp120 with CD4 molecules.

SUMMARY OF THE INVENTION

According to one feature of the present invention, there is provided a monoclonal antibody or fragment thereof capable of specifically binding to a glycoprotein antigen having a molcular weight of 120,000 dalton and located at the envelope of human T-lymphotropic virus Type III (HTLV-III) and lymphoadenopathy associated virus (LAV) and capable of substantially neutralizing said viruses.

Preferably the monoclonal antibody has the following characteristics:
(a) classified into $IgG_1$ class;
(b) capable of binding to the surfaces of a cell infected with HTLV-III virus thereby inhibiting the formation of syncytia induced from the infected cells and uninfected target T cells;
(c) capable of binding to a precursor of a glycoprotein antigen having a molcular weight or 160,000 dalton;
(d) capable of binding to an epitope located within amino acid sequence of 308 to 331 of HIV gp160, when determined with reference to Ratner, I., et al, Nature, 313, 277–284 (1985).

DESCRIPTION OF SPECIFIC EMBODIMENTS

The antibodies of the present invention may be prepared by immunizing a mammal, for example, a mouse, guinea pig or rabbit with a virus protein obtained from HTLV-III-producing cells, fusing the resultant spleen cells with myeloma cells of a mammal, for example, a mouse, and culturing the resultant hybridoma cells.

Although any and all cells which are capable of producing HIV when cultured may be used for the purpose of the present invention, it is preferred to use $H9/HTLV-III_B$ which is disclosed in JP-A-500767/86 (WO85/04897) and which was deposited with the American Type Culture Collection as ATCC CRL, No. 8543.

Culturing of HIV-producing cells and the recovery of HIV may be effected with reference, for example, to JP-A-285756/86 which disclose the characteristics and purification methods for the protein components of HIV, in particular, those of envelope protein.

For example, immunization of a mouse may be effected by administering hypodermically, intravenously or abdominally, purified HTLV-III viruses together with a suitable adjuvant, for example, Freund's complete adjuvant, alminium hydroxide gel or pertussis vacine.

HTLV-III may be adminstered 3–5 times at 0.05–0.1 mg per dose at intervals of 1–3 weeks. 3–7 days after the final immmunization, the speen is removed from the mouse in conventional manner.

Myeloma cell lines of mouse origin may be used for fusion. Examples of preferred cell lines include 8-azaguanine-resistant murine myeloma cell lines such as P3-X63-Ag8-U1 (P3-U1) from BALB/c strain [European J. Immunology 6, 511–519 (1976)]; SP2/0-Ag14 (SP-2) [Nature 276, 269–270 (1978)]; P3-X63-Ag8.653 (653) [J. Immunology 123, 1548–1550 (1979)], P3-X63-Ag8 (X63) [Nature 256, 495–497 (1975)] and the like. The cell lines may be subcultured, for example using an 8-azaguanine medium viz. a medium prepared by adding 8-azaguanine (15 $\mu$g/mi) to a normal medium [prepared by adding to RPM1-1640 medium, glutamine (1.5 mM), 2-mercaptoethanol ($5\times10^{-5}$M), gentamycin (10 $\mu$g/ml) and 10% FCS (fetal calf serum: commercial product of CSL, Australia)].

The cells are further subcultured for 3–4 days before fusion using a normal medium so as to ensure that the number of cells is greater than $2\times10^7$ on the date of hybridization. Hybridization may be effected in conventional manner as follows:

The above-mentioned myeloma cells and the spleen cells are well washed with MEM medium or with PBS and mixed together, the ratio of the number of spleen cells to the number of myeloma cells being preferably 5–10:1. The mixture is then centrifuged (1,200 r.p.m./5 min) to remove the supernatant. The pelleted cells are well loosened and then a mixed solution of polyethylene glycol 4000 (2 g), MEM medium (2 ml) and dimethyl sulfoxide (0.7 ml) is added in an amount of 0.2–1 ml per $10^3$ antibody-producing cells at a temperature of 37° C. with stirring. MEM medium (1–2 ml at a time) is added several times to the cell suspension at intervals of 1–2 minutes. After this the cell suspension is made up to 50 ml in total by adding MEM medium. The supernatant is removed from the culture by centrifugation (900 r.p.m./5 min). The cells are loosened and normal medium (100 ml of RPMI-1640 containing 10% FCS) is added to the cells. The cells are resuspended by gentle pipetting.

The cell suspension is poured into each well of a 24-well culture Plate (1 ml/well) for incubation at a temperature of 37° C. for 24 hours in a 5% $CO_2$ incubator. To each well of the plate is then added HAT medium (1 ml) [prepared by adding hypoxanthine ($10^{-4}$M), thymidine ($1.5\times10^{-5}$M) and aminopterine ($4\times10^{-7}$ m) to the normal medium] to continue the culturing for 24 hours further. 1 ml of the supernatant is removed from each well and replaced by the same amount of fresh HAT medium at an interval of 24 hours for a period of 2 days. The culturing is continued further at a temperature of 37° C. for 10–14 hours in a $CO_2$ incubator. When the grown colonies of the fused cells are observed in certain wells, 1 ml of the supernatant is removed from each of these wells and replaced by the same amount of fresh HT medium [prepared by omitting aminopterine from HAT medium]. The replacement of the medium by HT medium is continued further for 2 days at an interval of 24 hours.

After further culturing for 3–4 days using HT medium, part of the supernatant is collected from the culture to determine the titre of antibody capable of binding to the surfaces of $H9/HTLV-III_B$ cells by the fluorescein antibody method as follows:

Fluorescein antibody method:

$H9/HTLV-III_B$ ($H9/III_B$) cells or uninfected H9 cells ($5\times10^5$) are suspended in the supernatant of the test culture for incubating at a temperature of 4° C. for 30 minutes. The cells are washed twice with PBS containing BSA (2%) and azide (0.1%) (hereinafter referred to as PBS-BSA-Az). To the washed cells are then added 100 $\mu$l of anti-mouse IgG (Sigma), the IgG being labelled with FITC (fluorescein isothiocyanate) and diluted with PBS-BSA-Az at a ratio of 1:40. The mixture is incubated at a temperature of 4° C. for 30 minutes. After washing three times with PBS-BSA-Az, the reaction mixture is fixed using PBS containing paraform-aldehyde (0.1%).

The antibody reactivity is determined by the use of laser flow cytometry (Spectrum III, commercial product of Ortho niagnostics Inc.) with reference to the fluorescence intensity of fluorescein.

A clone exhibiting the highest binding ability to the surfaces of H9/HTLV-III cells is selected and subcloned to obtain the desired hybridoma cells.

Hybridoma 54/CB1, a hybridoma cell exhibiting the highest productivity among the resultant hybridoma cells was deposited with the European Collection of Animal Cell Cultures located at Portondown, Salisbury, Wilts, England on 14th May 1987 and designated as 54/CBI ECACC No. 87051401.

The preparation of monoclonal antibodies from the hybridoma may be effected, for example, as follows:

Pristane [2,6,10,14-tetramethylpentadecane: 0.5 ml] is abdominally given to a nude mouse (female; 8–10 weeks old). Two weeks after the inoculation of the pristane-treated mouse, the hybridoma cells are abdominally administered in an amount of 2–4×10$^6$ cells. 10–21 days after this, ascites tumour is induced by the hybridoma cells. The ascitic fluid is collected from the mouse and centrifuged (3000 r.p.m./5 min) to remove solids. After salting-out with ammonium sulfate (50%), the solution is subjected to dialysis against 0.04M phosphate-buffered solution containing 0.03M NaCl (pH 8.0). The resultant residue is passed through a column packed with DE52 (commercial product of Whatman, U.S.A.) to collect IgG fractions which may be used as purified monoclonal antibody. The isotype of the monoclonal antibody may be determined by Ouchterlony's method (double diffusion test) [see "Menekigaku Jikken Nyumon, Seibutu-kagaku Jikkenho 15, page 74 (1981)", published by Gakkai Shuppan Centre, Japan].

Quantitative determination of protein may be effected by the Folin's method and with reference to an optical density at 280 nm [1.4 (OD$_{280}$)≈immunoglobulin 1 mg/ml].

The characteristics of the monoclonal antibody of the present invention may be determined by the Western blotting method, the radioimmunoprecipitation method, the cross-precipitation method and the detection of the digest pattern using endoglycosidase, as described in the example hereinafter.

It has been confirmed that the monoclonal antibody of the present invention is capable of inhibiting both cell-to-cell infection, as identified by the formation of syncytia, and cell-free infection.

The monoclonal antibodies of the present invention may be used for the diagnosis, prevention and treatment of AIDS as well as for the purification of AIDS virus antigen.

Thus, it would be possible to inhibit growth of the viruses in human hosts or to inhibit further infection by the viruses by the use of the monoclonal antibody of the present invention, and also the monoclonal antibody of the present invention may be used for treating AIDS.

In this respect, the monoclonal antibodies of the present invention may be effective for preventing HIV infection of uninfected T4 cells due to their strong neutralizing ability.

Thus, the present invention further relates to a pharmaceutical composition comprising, in addition to one or more pharmaceutically inert excipients and/or carriers, an effective amount of at least one monoclonal antibody as hereinbefore described.

It is also possible to use the monoclonal antibodies of the present invention for purification of HIV envelope antigen, for example when bound to a suitable carrier material. The invention therefore includes within its scope an antibody-affinity carrier wherein a monoclonal antibody as hereinbefore described is bound to a suitable carrier material.

The following example illustrates the present invention in detail, wherein the treatments were effected at room temperature unless otherwise specified.

BRIEF DESCRIPTION OF THE DRAWINGS

FIG. 2 shows the Patterns of the antibodies of the present invention detected by electrophoresis.

FIG. 3 shows the inhibition of syncytia induced by H9/HTLVIIIB cells by the 0.5β antibody. FIG. 3A and FIG. 3F are control panels of CEM cells alone; FIG. 3B and FIG. 3G are control panels of H9/HTLV-III$_B$ cells alone; FIG. 3C and FIG. 3H show syncytia resulting from preincubation with 50 ug of MOPC 21 per ml; FIG. 3D and FIG. 3I show syncytia resulting from preincubation with 50 ug of 0.5β antibody per ml; FIG. 3E and FIG. 3J show syncytia resulting from preincubation with 5 ug of 0.5β antibody per ml; and FIG. 4 shows a pattern of elution obtained by the present antibody when used for purifying the envelope antigen of H9/HTLV-III$_B$ origin.

EXAMPLE

Figure 1A:
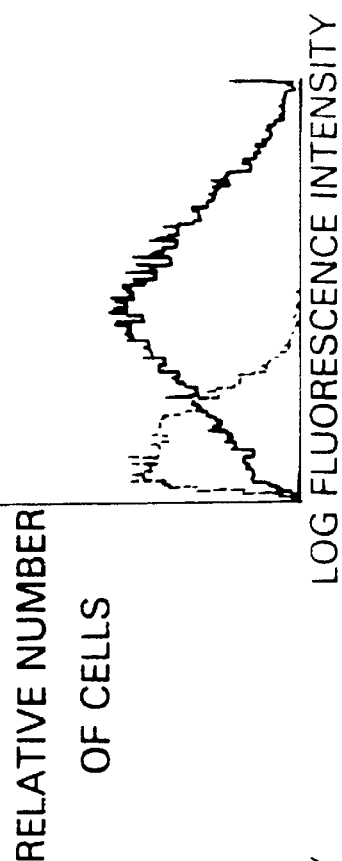
FIG. 1A shows the reactivity of the antibody of the present invention against H9 cells infected with HTLVIIIB.
Figure 1B:
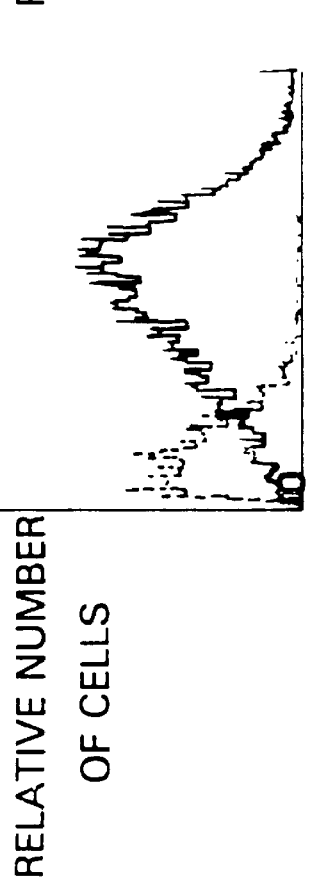
FIG. 1B shows the reactivity of the antibody of the present invention against CEM cells infected with LAV-1.
Figure 1D:
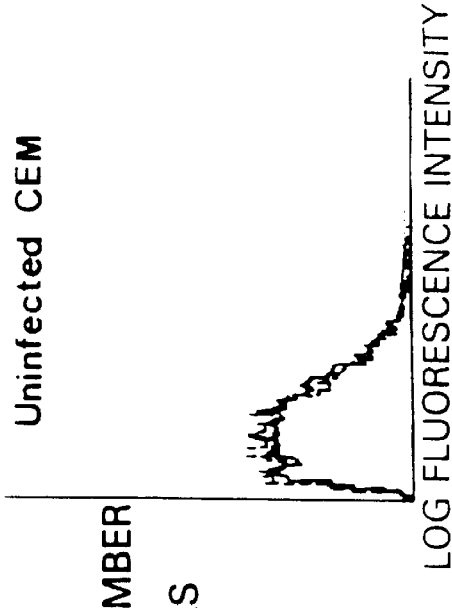
FIG. 1D shows the reactivity of the antibody of the present invention against uninfected CEM cells.
Figure 1C:
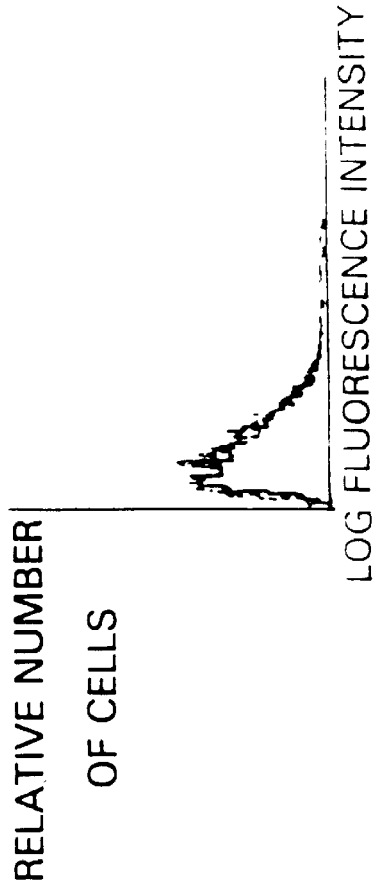
FIG. 1C shows the reactivity of the antibody of the present invention against uninfected H9 cells.

1) Preparation of antigen:

H9 cells infected with HTLV-III$_B$ [Science 224, 497–500 (1984)] (hereinafter referred to as H9/HTLV$_B$) were cultured using RPMI 1640 medium containing 10% FCS in an incubator containing 5% CO$_2$ at a temperature of 37° C. for 24 hours.

In a similar manner to that described in the above-mentioned article, the supernatant of the medium was used for purifying the viruses. The purified viruses were inactivated by heating for one hour at a temperature of 56° C. and were used as an antigen for the primary immunization.

A fraction of glycoprotein of the viruses prepared in the following manner was used as a booster dose for intensifying the immunization:

The H9/HTLV-III$_B$ cells cultured by the above-mentioned method were washed three times with PBS and were then centrifuged (2000 r.p.m./5 min) to obtain cell pellets. The cells (2×10$^8$) were washed three times with PBS saline (0.015M); (pH 7.2). The cells were solubilized by adding a cell lysing buffer solution [prepared by omitting sodium deoxycholic acid from RIPA buffer solution (5 ml) containing 1% Triton-X, 0.5% sodium salt of deoxycholic acid, 0.1% SDS, 0.15M NaCl and 0.05M Tris-HCl and having a pH of 7.2] and incubated at a temperature of 4° C. for 60 minutes. The lysate was centrifuged (3000 r.p.m./10 min). The supernatant was collected and heated at a temperature of 56° C. for one hour. The resultant solution was added to FCS-Sepharose [prepared by binding fetal calf serum (20 mg/ml) to Sepharose 4B (1 ml)] and reacted at a temperature of 4° C. overnight (for about 12 hours). The reaction solution was centrifuged (3000 r.p.m./10 min) to obtain a supernatant which was then used as the test sample.

The sample solution (1 ml) was added to ConA-Sepharose (0.5 ml; commercial product of Sigma) and was incubated at a temperature of 4° C. overnight (for about 18 hours). The material was put into a column and, after washing with PBS, elution was effected using α-methyl-D-glucoside (0.5M; 3 ml). The effluent was collected and divided into small fractions (each 0.5 ml).

Sera were collected from hemophiliac patients who were the healthy carriers of HIV. From the collected sera one exhibiting the highest antibody titre against the envelope was selected by the Western blotting method and purified to obtain IgG fraction. Each lysate was added to Sepharose 4B bound with the purified IgG (5 mg/ml) [hereinafter referred to as anti-HIV-Sepharose] and was incubated at a temperature of 4° C. for more than 4 hours. The anti-HIV-Sepharose was put in a column, washed with PBS and eluted with 0.2M glycine-buffered solution (pH 2.7). The eluent containing 0.1 mg/ml of the antigen was used as a booster for intensifying the immunization.

2) Preparation of hybridoma:

Purified viruses were inactivated by heating at a temperature of 56° C. for one hour. The viruses (0.1 ml) were mixed with Freund's complete adjuvant (0.1 ml) and used for primary immunization of a Balb/c mouse (purchased from Kuroda Dobutsu K.K., Japan). Then a purified antigen solution of virus glycoprotein (each 0.1 ml) mixed with Freund's incomplete adjuvant (each 0.1 ml) was used as a booster dose and was intraperitoneally given to the animal 3 times at intervals of 2 weeks. 3 days after the final immunization, the spleen cells were collected from the mouse in conventional manner. The spleen cells were mixed with P3-X63-Ag8 (X63) [Nature, 256, 495–497 (1975)], the ratio of the number of spleen cells to the number of myeloma cells being 1:5. The mixture was centrifuged (1200 r.p.m./5 min), followed by removal of the supernatant. The pelleted cells were well loosened and a mixed solution (0.2–1 ml/$10^3$ of antibody-producing cells) of polyethyleneglycol 4000 (PEG-4000; 2 g), MEM (2 ml) and dimethylsulfoxide (0.7 ml) was added to the antibody-producing cells with stirring. After this, MEM (1–2 ml at a time) was added several times to the mixture at intervals of 1–2 minutes, followed by addition of MEM to make up to 50 ml in total. The cell suspension was centrifuged to remove the supernatant. The cell pellets were loosened and a normal medium [100 ml: prepared by adding 10% FCS to RPMI-1640] was added thereto. The cells were loosened by gentle pipetting.

The cell suspension was poured into each well of 24-well culture plates in an amount of 1 ml per well, followed by incubating at a temperature of 37° C. for 24 hours using a $CO_2$ incubator. After adding to the culture plate a HAT medium [prepared by adding to a normal medium, hypoxanthine ($10^{-4}$M), thymidine ($1.5\times10^{-5}$M) and aminopterine ($4\times10^{-7}$ m)], the culturing was effected further for 24 hours. For 2 days after this, the supernatant (1 ml) was removed, and the same amount of fresh HT medium was added to each well at an interval of 24 hours. The culturing was effected further for 10–14 days at a temperature of 37° C. using an $CO_2$ incubator.

When the presence of fused cells (about 300) grown in the form of colonies in certain wells was found, on each occasion, the supernatant (1 ml) was removed from the well and replaced by fresh HT medium (1 ml: prepared by omission of aminopterine from HAT medium). Such a replacement by HT medium was effected further for 2 days at an interval of 24 hours.

After culturing for 3–4 days using HT medium, part of the supernatant was collected from each of the above-mentioned cultures for assaying the ability to bind to the surfaces of H9 cells infected with HTLV-III$_B$ by the above-mentioned fluorescein antibody method. A clone exhibiting the highest binding activity was designated as 54'C which was further subjected to subcloning to select a subclone designated as 54'CB1 which grew vigorously to exhibit the highest productivity of the antibody.

3) Preparation of monoclonal antibodies by the use of 54'CB1:

Hybridoma cells of 54'CB1 prepared by method (2) were abdominally given to Balb/c mice [pristane-treated; 8 weeks old] in an amount of $4\times10^6$ cells/mouse. 10–21 days after this, ascites tumour was induced by the hybridoma cells. From the host mice of the ascites tumour, ascitic fluid was collected in an amount of 5–10 ml/mouse. After removal of solids from the ascites by centrifugation (3000 r.p.m./5 min), the salting-out of the supernatant was effected using ammonium sulfate (40%). The solution was dialyzed against 0.04M phosphate-buffered solution containing NaCl (0.03M) and having a pH of 8.0. The residue was passed through a column packed with DE52 (bed volume 50 ml; commercial product of Whatman) at a flow rate of 20–30 ml per hour to collect IgG fractions which were used as purified monoclonal antibody (designated as 0.5β antibody).

4) Surface reactivity of 0.5β antibody:

The reactivity of the resultant antibody with the surfaces of H9 or CEM cells infected with HTLV-III$_B$ or LAV-1 was determined by the above-mentioned fluorescein antibody method to obtain results as shown in FIG. 1. The present antibody is reactive with the surfaces of H9 or CEM cells infected with HTLV-III$_B$ or LAV-1, but is not reactive with uninfected cells.

Figure 2A:
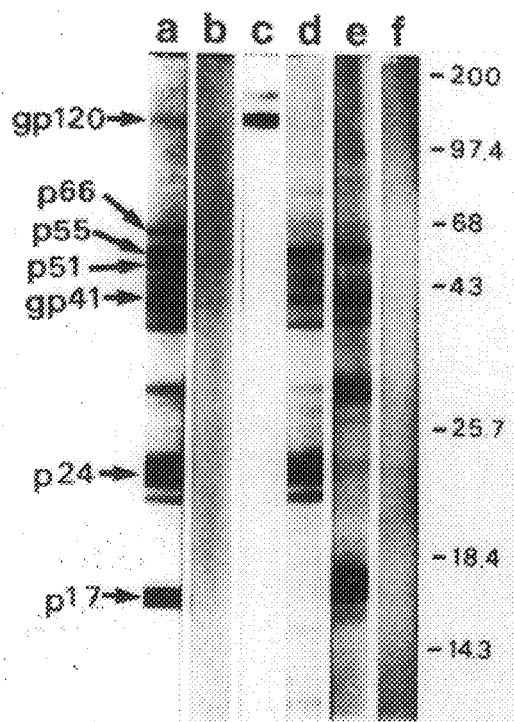
FIG. 2A shows the pattern detected by the Western blotting method.
Figure 2B:
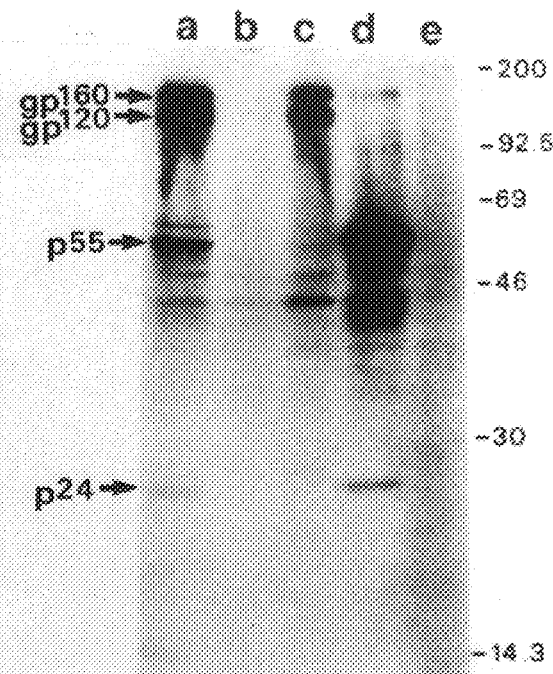
FIG. 2B shows the pattern obtained by the radioimmunoprecipitation method.
Figure 2C:
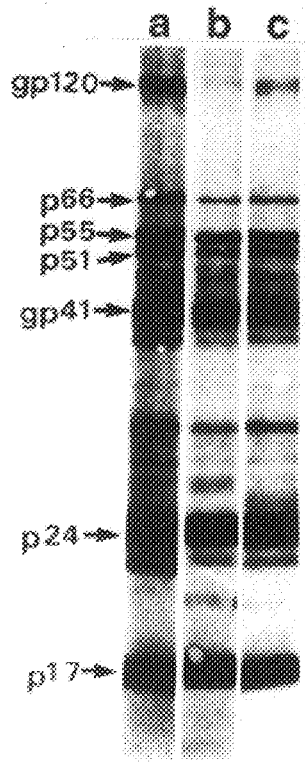
FIG. 2C and FIG. 2D show respectively the patterns detected by the cross-precipitation method.
Figure 2D:
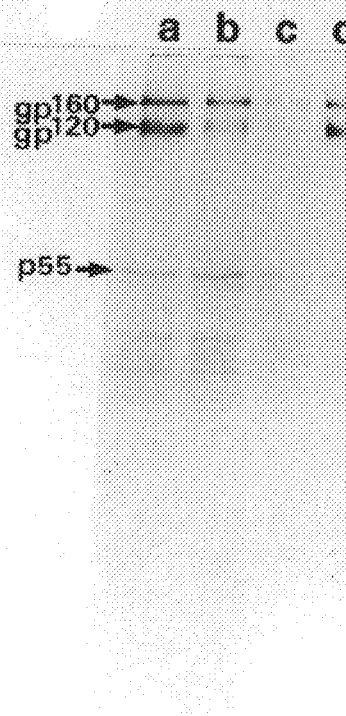
Figure 2E:
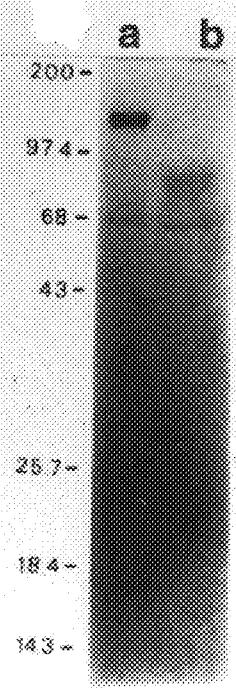
FIG. 2E shows the pattern of digestion by endoglycosidase H.

5) Binding characteristics of 0.5β antibody:

The antibody of the present invention was assayed by the Western blotting method (see FIG. 2A), the radioimmuno-precipitation method (see FIG. 2B), the cross-precipitation method (see FIGS. 2C and 2D) and by the digest pattern obtained using endoglycosidase H (see FIG. 2E). As a result, it has been found that the present antibody is capable of specifically binding to gp120 of the envelope protein located at the HIV envelope.

A. Western blotting method:

With reference to Towbin, H., Stachelin, T. and Gordon, J. [Proc. Natl. Acad. Sci. USA 76, 4350–4354 (1979)], the Western blotting method was carried out in the following manner:

Purified HTLV-III$_B$ viruses [prepared by the method disclosed in Science 224, 497–500 (1984)] were subjected to electrophoresis using 12% SDS-PAGE [disclosed in Nature 227, 680–685 (1970)]. The gel was put onto a nitrocellulose membrane to transfer the viruses onto the surface of the membrane. The membrane was cut into strips having a width of 0.4–0.6 cm. On each occasion, the strips were put into one of the following antibody solutions (a)–(f) for incubation at room temperature for 4 hours:

(a) serum obtained from a hemophiliac patient having a positive activity against anti-HIV antibody;
(b) human serum (control);
(c) 0.5β antibody;
(d) VAK5 (anti-p24) monoclonal antibody produced by the hybridoma obtained by immunizing mouse with p24, a gag antigen of HTLV-III$_B$, which is capable of recognizing p24 and its precursor [Jpn. J. Cancer Res. (Gann) 78, 235–241 (1987)];
(e) 52E5 (anti-p17) monoclonal antibody [monoclonal antibody produced by the hybridoma obtained by immunizing HTLV-III$_B$, which is capable of recognizing p17 and its precursor, said p17 being one of the gag proteins of HLTV-III]; and
(f) mouse IgG$_1$ antibody (MOPC21) as control [Litton Biogenetics Inc. Catalogue No. 8401-03].

Samples (a) and (b) were diluted with PBS-BSA-Az (1:50) and Samples (d)–(f) were diluted with ascitic fluid (1:500) and treated in the following manner at room temperature unless otherwise specified.

The incubated strips were washed three times with PBS and incubated for 2 hours in a diluted solution (1:750) of biotin-conjugated anti-human or anti-mouse IgG antiserum (commercial product of TAGO). The strips were washed three times with PBS and immersed in a diluted solution (1:1000) of avidin conjugated with hores radish-peroxdase (commericial product of Sigma) for incubation for one hour. After this, the material was washed three times with PBS and treated with a colour-developing reagent containing 4-chloro-1-naphthol (commercial product of BioRad). The results are shown in FIG. 2A, in which (a)–(f) correspond respectively to the above mentioned antibodies. FIG. 2A indicates that 0.5 β antibody is capable of recognizing the envelope of HTLV-III$_B$ having a molecular weight of 120 Kd.

B. Radioimmunoprecipitation method:

H9/HTLV-III$_B$ ($2 \times 10^7$ cells) was labelled with $^{35}$S cysteine by incubating for 4 hours in a solution containing $^{35}$S cysteine (100 μCi/ml). After washing with PBS, the cells were put into RIPA buffer solution (0.5 ml). Soluble cell lysate was prepared by breaking the cell membrane using a vortex, followed by centrifugation (10000 r.p.m./one hour).

The lysate was subjected to reaction with normal human IgG (500 μg) [purified using Protein A Sepharose, with reference to a guidebook of affinity chromatography (Principles & Methods, p48–52, published by Pharmacia Fine Chemicals AB.)] for 18 hours. The reaction mixture as centrifuged (10000 r.p.m./10 min) to collect the supernatant which was used as a sample solution. The sample solution (40 μl) was mixed with immuno-beads [prepared by binding, on each occasion, 40 μg of one of the following antibodies (a)–(e) with 20 μl of Sepharose 4B], incubated at a temperature of 4° C. for 4 hours.

(a) serum obtained from a patient having a positive activity against anti-HIV antibody (control);
(b) human serum (control);
(c) 0.5β antibody;
(d) VAK5 (anti-p24) (control);
(e) MOPC21 (control).

After washing 4 times with PBS, the beads were suspended in a sample buffer (50 μl) and heated for 2 minutes under reflux to elute the bound protein. On each occasion, the supernatant was subjected to electrophoresis using 12% SDS-PAGE and assayed by autoradiography in conventional manner. The results shown in FIG. 2B indicate that 0.5β antibody is capable of recognizing both gp120 which is a mature protein and gp160 which is a precursor of gp120.

In this case, a mixture of 0.75M tris-HCl buffered solution (8.3 ml; pH 6.8), 10% SDS (20 ml), glycerol (10 ml), 2-mercaptoethanol (5.0 ml), H$_2$O (6.7 ml) and bromophenol blue (1 mg) was used as a sample buffer solution (X2) [Laemmli, U.K., Nature, 227, 680–685 (1970)].

C. Cross-precipitation method:

HTLV-III$_B$ was purified by the sucrose density-gradient ultracentrifugation to collect the active fraction having a specific gravity of about 1.16. The viruses were inactivated by heating at a temperature of 56° C. for one hour, followed by disruption with 0.5% NP40 to obtain purified viruses. The purified viruses (10 μl) were put in RIPA buffer solution (40 μl) and incubated together with Sepharose 4B bound to 0.5β antibody or Sepharose 4B bound to MOPC21 (prepared in a similar manner to that described above) at a temperature of 4° C. overnight (for about 18 hours). The reaction solution was centrifuged (5000 r.p.m./5 min) to give a supernatant, from which the following test samples were prepared:
(b) supernatant pre-treated with 0.5β Sepharose;
(c) supernatant pre-treated with MOPC21-Sepharose used as control; and
(a) untreated.

On each occasion, the sample was subjected to electrophoresis using 12% SDS-PAGE and blotted onto a nitrocellulose membrane. The membrane was subjected to reaction with the serum of a healthy host of HIV (diluted×100). The colour of the reaction product was developed by the method of 2-A using biotin-avidin-peroxidase. It has been observed that by treating with 0.5β antibody, the reactivity of envelope gp120 with the serum of the patient decreased, while the reactivity of control samples was not significantly changed. With regard to the reactivity with other proteins, no difference was found between the sample treated with 0.5 β antibody and the control sample.

D. Cross-precipitation method:

A similar procedure to that described in C as above was carried out using a lysate of H9/HTLV-III$_B$ labelled with $^{35}$S cysteine instead of purified viruses in the following manner:

Part of lysate supernatant of H9/HTLV-III$_B$ labelled with $^{35}$S cysteine was incubated together with Sepharose 4B bound to 0.5 β antibody or Sepharose 4B bound to MOCP21 prepared in a similar manner to that described above at a temperature of 4° C. overnight (for about 18 hours). The mixture was centrifuged (5000 r.p.m/5 min) to obtain the supernatant, which was designated as a sample treated once. Similarly, this sample was incubated for 4 hours and centrifuged to obtain a test sample treated twice.

On each occasion, the supernatant of part of the sample of lysate treated once or twice or the supernatant of part of untreated sample was subjected to reaction with an anti-HIV-IgG Sepharose [Sepharose bound to IgG having anti-HIV antibody activity] at a temperature of 4° C. for 4 hours. The reaction mixture was washed with a RIPA-bufferted solution 4 times, eluted using a sample buffer solution, treated with 12% SDS-PAGE and assayed by conventional autoradiography in a similar manner to that described in 2-B as decribed hereinbefore.

The results are shown in FIG. 2D, which indicates as follows:

(b) When Separose 4B bound with 0.5β antibody cleared the sample once, gp120 was significantly decreased; and (c) when cleared twice, both gp120 and gp160 almost diappeared;

(d) On the other hand, when the control IgG$_1$ cleared the lysate twice, a decrease of both gp120 and gp160 was not noted.

The result from untreated sample (control) is also shown in (a).

E. Digest pattern by using endoglycosidase:

0.5% NP40 was added to purified HTLV-III$_B$ (10 μl). The mixture was incubated at a temperature of 4° C. for 24 hours to disrupt the cells, followed by dialysis against 0.1M sodium citrate (pH 5.5). Endoglycosidase H (commercial product of NEN; 0.25 U) was added to the disrupted viruses which were then incubated at a temperature of 37° C. for 3 hours to digest the viruses.

On each occasion, one sample selected from (b) digested HTLV-III$_B$ and (a) HTLV-III$_B$ treated with buffered solution was subjected to electrophoresis using 12% SDS-PAGE and blotted onto a nitrocellulose membrane. In a similar manner to that described in A hereinbefore, colour was developed by using 0.5β antibody to develope colour on the strips of the nitrocellulose membrane. The results are shown in FIG. 2E, which indicates that 0.5β antibody is also reactive with protein portion (70–84 Kb), from which sugar chains were cut off by endoglycosidase.

6) Inhibiting activity of 0.5β antibody against the formation of syncytia by the action of HTLV-III$_B$:

H9/HTLV-III$_B$ ($2.5 \times 10^4$ cells) was incubated together with 50 μg/ml of MCOP 21 ascites (FIGS. 3C, 3H), 50 μg/ml of 0.5β ascites (FIGS. 3D, 3I) or 5 μg/ml of 0.5β ascites (FIGS. 3E, 3J) at room temperature for 30 minutes in RPMI-1640 medium (100 μl) containing 10% FCS, to which was then added $5 \times 10^4$ CEM cells (50 μl) for culturing at a temperature of 37° C. for 18 hours using an incubator containing 5% $CO_2$. Similarly, each of CEM (FIGS. 3A, 3F) and H9/HTLV-III$_B$ (FIGS. 3B, 3G) was cultured and used as control. After culturing, an inverted microscope was used to take photographs. FIGS. 3A–E (X 150) and FIGS. 3F–J (X 60) were taken after culturing for 18 hours and a further culturing for 3 days respectively. It was found that the formation of syncytia (FIG. 3C) and the formation of cell clumps (FIG. 3H) in the control samples were completely inhibited in the presence of 50 μg/ml of 0.5β antibody (FIGS. 3D, 3I). The formation of smaller numbers of syncytia (FIG. 3E) and the formation of smaller cell clumps (FIG. 3H) were observed in the presence of diluted 0.5β antibody (5 μg/ml). In this case, it was observed that the cells did not form larger clumps and scattered around the syncytia and the cell clumps. From this fact, it appears that the use of 50 μg/ml of 0.5β antibody effectively inhibits infection between the cells, while the use of 5 μg/ml of 0.5β antibody gave partial inhibition. On each occasion, the ascites was inactivated at a temperature of 56° C. for one hour before use.

7) Neutralizing activity of 0.5β antibody:

In a similar manner to that disclosed in JP-A-500767/86 and JP-A-28756/86, HTLV-III$_B$ viruses (2–5×10$^8$/ml) were collected by ultracentrifugation (32,000×g, 3 hours) of the supernatant of a culture of H9/HTLV-III$_B$. On each occasion, the viruses (20 μl) and 0.5β antibody (20 μl) at different dilution ratios were put into each well of a 96-well round bottom culture plate for incubation at a temperature of 4° C. for one hour, followed by further incubation at room temperature for 15 minutes.

H9 cells (4×10$^4$) were treated at room temperature for 20 minutes using polyburen (2 μg/ml), and washed with RPMI-1640 medium. Then the cells were transferred to another RPMI-1640 medium (200 μl) containing 20% FCS, penicillin (50 U/ml) and streptomycin (50 μg/ml) for incubation at a temperature of 37° C. for 5–6 days.

The presence of HTLV-III$_B$ p24 antibody in H9 cells was assayed by the fluorescein antibody method to calculate the titre of the neutralizing antibody [Nature 316, 72–74 (1985)].

The results are shown in Table 1. In this table, the neutralizing activity of the antibodies is expressed by ng/ml of purified IgG or by the reciprocal number of the dilution ratio of the serum and ascites.

TABLE I

| | Neutralizing antibody titre | |
|---|---|---|
| Purified 0.5β | 0.5β in ascites | Human serum (positive) |
| 100 ng/ml | >6250 | 280 |

0.5β antibody of the present invention exhibits a neutralizing activity at low concentration such as 100 ng/ml of purified antibody. In the form of ascites, a 100% neutralizing activity was observed at a dilution ratio of 1:6250.

8) Purification of envelope antigen from H9/HTLV-III$_B$ cells:

H9/HTLV-III$_B$ was cultured and treated to obtain a pellet in a similar manner to that described in (1) hereinbefore. The pellet (5×10$^7$ cells) was suspended in RIPA buffer (2.5 ml) and incubated at a temperature of 4° C. for 60 minutes to obtain a cell lysate. The cell lysate was centrifuged (3000 r.p.m./10 min) to remove solids. The supernatant was heated at a temperature of 56° C. for one hour to inactivate HTLV-III$_B$. The inactivated cells were subjected to reaction with about 0.5 ml of FCS-beads [Sepharose 4B bound to 10% FCS] at a temperature of 4° C. for 18 hours and centrifuged (5000 r.p.m./5 min).

Non-specific adsorbates were adsorbed onto the FCS-beads.

The supernatant was mixed with 0.5β antibody-bound Sepharose 4B beads (200 μl) and incubated at a temperature of 4° C. for 4 hours. After completion of the reaction, the beads were packed into a column and washed with 4 ml of PBS (pH 7.2) and 2 ml of HSB [0.02M phosphate-buffered solution containing 0.5M NaCl; pH 7.2). Elution was effected using glycine-HCl (4 ml; pH 2.7) containing 0.15M NaCl. Immediately after this, the eluent was neutralized with Tris-HCl (pH 10). From each fraction (0.5 ml), 10 μl was collected and smeared into 2 wells of a ELISA plate Imuron I (commercial product of Dyantech Laboratories, U.S.A.). The sample was incubated at a temperature of 4° C. overnight in 0.09 ml of 0.1M carboxylic acid buffered solution (pH 9.8).

The ELISA method was carried out overnight to detect the eluted fraction, by which reaction with 0.5β antibody (X1500) was effected, followed by reaction with alkaline phosphatase-conjugated anti-mouse IgG to develop colour. In FIG. 4 purified antigen is shown by a single peak.

I claim:

1. A monoclonal antibody or fragment thereof having the following characteristics:
   a) which specifically binds to a glycoprotein antigen having a molecular weight of 120,000 daltons and located in the envelope of HTLV-III (HIV-I) virus;
   b) which specifically neutralizes
      (i) infection by cell-free virions in vitro and
      (ii) cell-to-cell infection of said virus in vitro by being capable of binding to the surface of a cell infected with HTLV-III (HIV-I) virus thereby to inhibit the formation of syncytia induced from infected cells and uninfected cells;
   c) which specifically binds to a precursor of a glycoprotein antigen, said precursor having a molecular weight of 160,000 daltons;
   d) which specifically binds to an epitope located within amino acid sequence of 308 to 331 of HTLV-III (HIV-1) gp160;
   e) which is classified as IgG$_1$; and
   f) wherein the antibody is the 0.5β monoclonal antibody produced by the 54/CBI hybridoma (ECACC 87051401).

2. Hybridoma 54/CBI, ECACC No. 87051401.

3. A composition, which comprises as active ingredient a monoclonal antibody or a fragment thereof as claimed in claim 1, together with at least one member selected from the group consisting of a pharmaceutically acceptable carrier and an excipient.

* * * * *